United States Patent
Hu

(10) Patent No.: US 9,038,625 B2
(45) Date of Patent: May 26, 2015

(54) LIQUID SPRAY DEVICE

(71) Applicant: Sheng-Pin Hu, Taipei (TW)

(72) Inventor: Sheng-Pin Hu, Taipei (TW)

(*) Notice: Subject to any disclaimer, the term of this patent is extended or adjusted under 35 U.S.C. 154(b) by 262 days.

(21) Appl. No.: 13/759,233

(22) Filed: Feb. 5, 2013

(65) Prior Publication Data

US 2014/0216443 A1 Aug. 7, 2014

(51) Int. Cl.
*A61M 11/00* (2006.01)
*A61M 15/00* (2006.01)

(52) U.S. Cl.
CPC ......... *A61M 15/0085* (2013.01); *A61M 11/005* (2013.01)

(58) Field of Classification Search
CPC ............... A61M 15/0065; A61M 15/0085; A61M 11/007; A61M 15/0086; A61M 15/0023; A61M 11/003; A61M 11/002; A61M 15/025; A61M 15/008; A61M 15/0066; A61M 15/02; A61M 11/005; A61M 11/001; A61M 15/0043; A61M 15/0036; A61M 11/00; A61M 15/0091; A61M 15/06; A61M 16/00; A61M 16/10; A61M 11/04; A61M 11/06; B05B 17/0607; B05B 17/0615; B05B 12/12; B05B 12/122; B05B 17/0684; B05B 17/0661; B05B 17/06; B05B 7/00; B05B 7/26; B05B 17/04; B05B 17/0646; B05B 17/0669; A47K 5/1217; A61L 9/14; A61L 2/22; B67D 7/74
USPC ............ 128/200.16, 200.14, 200.18, 200.19, 128/200.23, 203.12, 200.21, 200.24, 128/202.21, 203.14, 203.26, 203.27; 222/566, 564, 52; 239/102.1, 102.2, 239/407, 338; 261/1, 78.2, DIG. 48, DIG. 65
See application file for complete search history.

(56) References Cited

U.S. PATENT DOCUMENTS

| | | | | |
|---|---|---|---|---|
| 5,908,158 | A | * | 6/1999 | Cheiman .................... 239/102.2 |
| 5,950,619 | A | * | 9/1999 | van der Linden et al. ......................... 128/200.16 |
| 6,527,151 | B1 | * | 3/2003 | Pavkov et al. ................ 222/566 |
| 6,629,646 | B1 | | 10/2003 | Ivri |
| 6,863,224 | B2 | | 3/2005 | Terada et al. |
| 2003/0200964 | A1 | * | 10/2003 | Blakley et al. .......... 128/200.23 |
| 2005/0011514 | A1 | * | 1/2005 | Power et al. ............ 128/200.14 |
| 2008/0245362 | A1 | * | 10/2008 | Moessis et al. .......... 128/200.16 |
| 2010/0206306 | A1 | * | 8/2010 | Feriani et al. ............ 128/203.12 |

FOREIGN PATENT DOCUMENTS

DE 102009001867 A1 3/2010

* cited by examiner

*Primary Examiner* — Annette Dixon
(74) *Attorney, Agent, or Firm* — Rabin & Berdo, P.C.

(57) ABSTRACT

A liquid spray device includes a container defining a reception space for receiving a liquid medicine therein, having a discharge outlet for discharging the liquid medicine to an exterior of the container; a spray module disposed in the discharge outlet, and connected electrically to a driving source such that the liquid medicine forcefully collides against the discharge outlet due to ultrasonic oscillation of the spray module and spraying out a plurality of mist droplets; and a particle sorter disposed downstream to a discharging direction of the liquid medicine, spaced from the spray module at a predetermined distance to permit once against collision of the liquid medicine during the discharging operation such that the mist droplets are sprayed out through the particle sorter in terms of a plurality of micro-mist droplets along the discharging direction.

9 Claims, 7 Drawing Sheets

LIQUID SPRAY DEVICE

BACKGROUND OF THE INVENTION

1. Field of the Invention

The present invention relates to a liquid spray device, more particularly to a liquid spray device for use in pleural inhalation therapy.

2. The Prior Arts

A liquid spray device is generally used in pleural inhalation therapy, such as asthma, includes a container for receiving a liquid medicine, which is sprayed out in term of a plurality of mist droplets. It is noted that the mist droplets should have a MMAD (mass median aerodynamic diameter) size smaller than 5 μm, only then the mist droplets can be breathed in or swallowed through the bronchioles in a human lung. The mist droplets sprayed out from the available liquid spray device should contain 50% of uniform droplets, each having a MMAD size less than 5 μm so as to permit these droplets to be breathed in by a patient or else result in waste of the liquid medicine. The known filter employed in the available spray device produces qualified and non-qualified mist droplets for the patient, thereby resulting in ineffective control of the given dose of liquid medicine to each patient.

In addition, a majority of the mist droplets sprayed out from the conventional liquid spray device fade away in the air, only a small amount of the mist droplets is breathed in by the patient concerned. Hence, the spilled or unused mist droplets cause environment pollution and waste of liquid medicine and exposing the healthy people to breathe the undesired mist droplets of liquid medicine.

U.S. Pat. No. 6,629,646 discloses a fluid injection device for ejecting fluid droplets in response to electrical signals comprises: an oscillating surface that has one or more tapered apertures, each aperture having a first and second opening. The first opening of each aperture is larger than the second opening. The first opening is in surface tension contact with the fluid to be ejected. The fluid interaction with the tapered aperture wall creates cycles of fluid compression and decompression inside the aperture, causing fluid to be drawn from the large opening and ejected out the small opening of the aperture. The device further includes a fluid supply nozzle that transports fluid to the oscillating surface at the larger opening of the aperture. A discharge valve controls the fluid supply. An electronic wave generator induces oscillation in the tapered aperture surface.

Another U.S. Pat. No. 6,863,224 discloses a liquid atomizing device including a bottom unit having a bottle section reserving a chemical liquid; a horn oscillating member to whose a distal end the liquid in the bottle section is fed; and a mesh member having a number of fine pores and mounted to an end surface of the distal end of the horn oscillating member in contact therewith. The bottle section is constituted of a large capacity section and a small capacity section in communication with the large capacity section through an opening opposing to the distal end. The small capacity section is formed such that the liquid is in contact with a point in the proximity of the contact section between the distal end of the horn oscillating member and the mesh member. The fluid dispensing operation is conducted without a special liquid feed means.

German Patent No. 102009001867 discloses a spray device including a driving unit for generating an oscillating energy; a polymer layer consisting of a plurality of apertures distributed at the bottom of the driving unit for generating fluid cycle in response to the oscillating energy, a tapered transmitting member connected to the polymer layer and having an opening corresponding to the apertures in the polymer layer, a circular oscillation member coupled electrically to the transmitting member for providing oscillation so that the liquid medicine on the polymer layer is sprayed out in form of micro mist droplets upon activation of the oscillation member.

In the above mentioned spray devices for pleural inhalation therapy, whether a metal mesh member is fixed and vibrated through the ultrasonic oscillator, as disclosed in U.S. Pat. No. 6,863,224, an alloyed micro sorter member is vibrated by ultrasonic metal ring (spray module), as disclosed in U.S. Pat. No. 6,629,646, or vibration of the polymer layer by the circular oscillation member, as disclosed in German patent No. 102009001867, to create a plurality of mist droplets depend on the aperture size and configuration of the filter member. Hence, the dimension of the plurality of mist droplets ranges from 0.5 ↑m to 50 μm. However, for the bronchioles of the human lung to breathe therethrough, the standard size of the mist droplets MMAD should be smaller than 5 μm and the mist droplets should occupies about 50% of the sprayed liquid. The abovementioned spray devices have the following disadvantages:

(a) In order to produce the mist droplets smaller than MMAD 5 μm, the micro pores in the mesh member should have a diameter equivalent to or less than 5 μm. It is expensive to construct the mesh member with less than MMAD 5 μm micro pores.

(b) Since only the mist droplets with less than MMAD 5 μm are breathed in by the bronchioles of the human lung, the remaining mist droplets vanish in the air, thereby causing waste of liquid medicine and resulting in insufficient of breathed in mist droplets of liquid medicine by the patient.

(c) Scatter of the mist droplets with greater than MMAD 5 μm in the air creates environmental pollution, which, in turn, can cause water pollution.

SUMMARY OF THE INVENTION

One objective of the present invention is to provide a liquid spray device having a particle sorter with micro pores which is adapted to spray out mist droplets of liquid medicine with a MMAD size smaller than 5 μm, thereby enhancing the price quantity of the spray device.

Another objective of the present invention is to provide a liquid spray device, in which, waste of liquid medicine is eliminated due to spraying out of mist droplets having a MMAD size greater than 5 μm, since extra amount of liquid medicine is required to produce the desired amount of mist droplets smaller than 5 μm.

Yet another objective of the present invention is to provide a liquid spray device, which eliminates the problem of sprayed out mist droplets with greater than MMAD 5 μm, thereby providing a hygienic environment.

The liquid spray device of the present invention includes a container defining a reception space for receiving a liquid medicine there in, the container having a discharge outlet for discharging the liquid medicine to an exterior of the container; a spray module disposed in the discharge outlet, and connected electrically to a driving source such that the liquid medicine forcefully collides against the discharge outlet due to ultrasonic oscillation of the spray module, thereby spraying out a plurality of mist droplets; and a particle sorter disposed downstream to a discharging direction of the liquid medicine, spaced from the spray module at a predetermined distance to permit once against collision of the liquid medicine during the discharging operation such that the plurality of mist droplets are sprayed out through the particle sorter in terms of a plurality of micro-mist droplets (MMAD less than 5 μm) along the discharging direction.

The liquid spray device of the present invention further includes a recycle system that is installed within the container, that is adapted to collect the plurality of mist droplets and that is adapted to automatically transfer the plurality of mist droplets back into the liquid medicine for collecting in the reception space of the container.

Preferably, the container has a first opening formed at a bottommost portion thereof and a second opening formed at a topmost portion thereof and in spatial communication with the reception space in the container.

The recycle system preferably includes a collection tube fastened to the container and having a lowest tube section proximate to and in spatial communication with said first opening and a connection pipe interconnecting the first and second openings such that in case than the discharge outlet is biased by pressure of the liquid medicine during the discharging operation, a siphon phenomenon is resulted due to vacuum of the reception space to draw the plurality of mist droplets collected at the lowest tube section back into the reception space via the first opening, the connection pipe and the second opening.

Preferably, the collection tube has a dispensing tube section inclined upward with respect to an axis of the discharging outlet of the container to facilitate flow back of the mist droplets into the lowest tube section of the collection tube.

In this embodiment, the particle sorter is planar, concave or convex with respect to the spray module. Preferably, the particle sorter has a surface area greater and/or smaller than that of the spray module. The particle sorter has an interior surface facing the spray module and formed with a plurality of recesses. Alternately, particle sorter has an interior surface facing the spray module and formed with a plurality of protrusions. The surface area of the interior surface, the number or size of the recess or the protrusions, and the predetermined distance between the particle sorter and the spray module can be adjusted depending on the required size of the micro mist droplets. For instance, the predetermined distance between the particle sorter and the spray unit can be adjusted to be equivalent to, less than or greater than the diameter of the particle sorter. The above mentioned adjustment is conducted during the manufacturing process and the user can not do the adjustment of ones own accord.

BRIEF DESCRIPTION OF THE DRAWINGS

Other features and advantages of this invention will become more apparent in the following detailed description of the preferred embodiments of this invention, with reference to the accompanying drawings, in which.

DETAILED DESCRIPTION OF THE PREFERRED EMBODIMENTS

Figure 1:
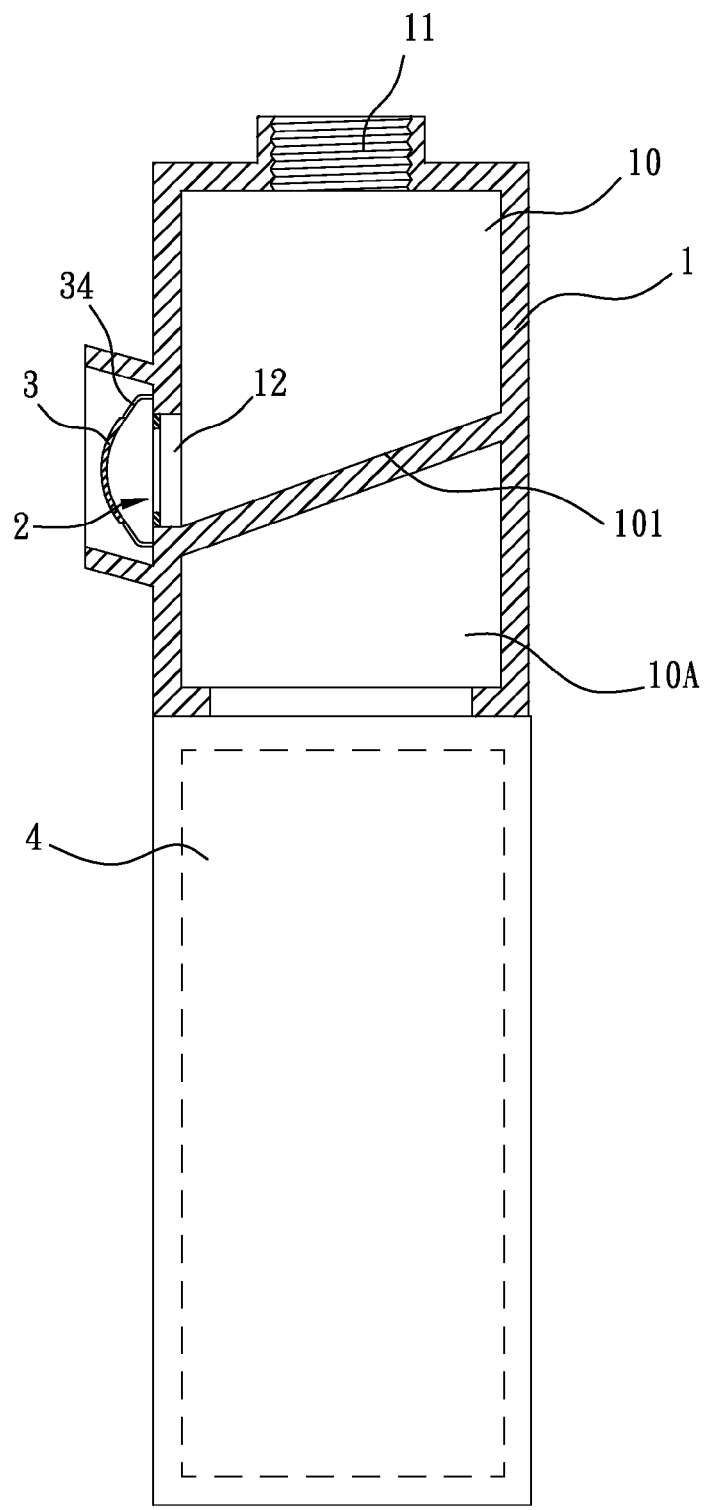
FIG. 1 shows a cross-sectional view of a liquid spray device of the present invention viewed from a front side thereof.
Figure 2:
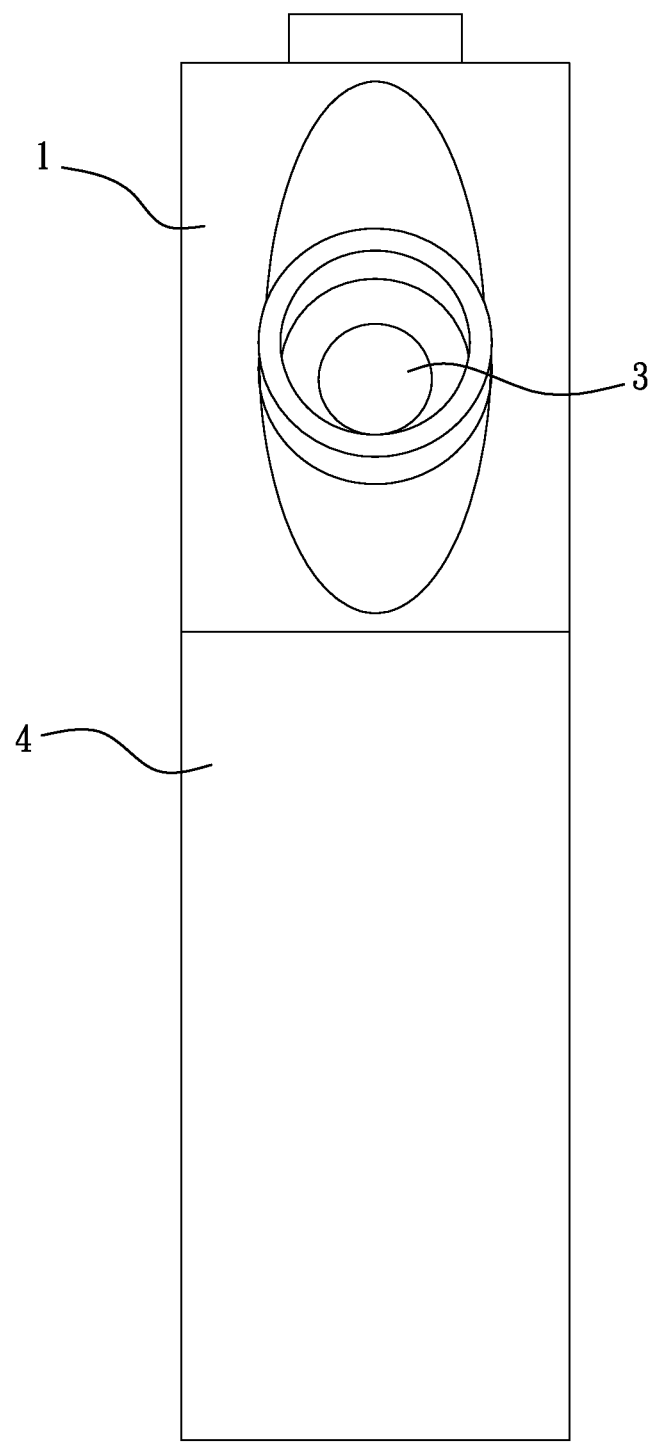
FIG. 2 shows a lateral plan view of the liquid spray device of the present invention.

Referring to FIGS. 1 and 2, wherein FIG. 1 shows a cross-sectional view of a liquid spray device of the present invention viewed from a front side thereof while FIG. 2 shows a lateral plan view of the liquid spray device of the present invention. As illustrated, the liquid spray device of the present invention includes a container 1, a spray module 2, and a particle sorter 3. The container 1 defines a reception space 10 for receiving a liquid medicine L (see FIG. 3) therein. The container 1 further has an inclined bottom 101, below which a lower reception space 10A is defined, and a drive source 4 is disposed below the inclined bottom 101 and in spatial communication with the lower reception space 10A. The container 1 further has a discharge outlet 12 with an appropriate diameter located adjacent to the lowest end of the inclined bottom 101 for discharging the liquid medicine L to an exterior of the container 1, and an inlet 11 at the topmost portion for filling the liquid medicine L into the reception space 10. After filling the liquid medicine L, the inlet 11 of the container 1 is hermetically sealed (not visible) to prevent spilling out of the liquid medicine L during formation of the mist droplets within the container 1.

Figure 3:
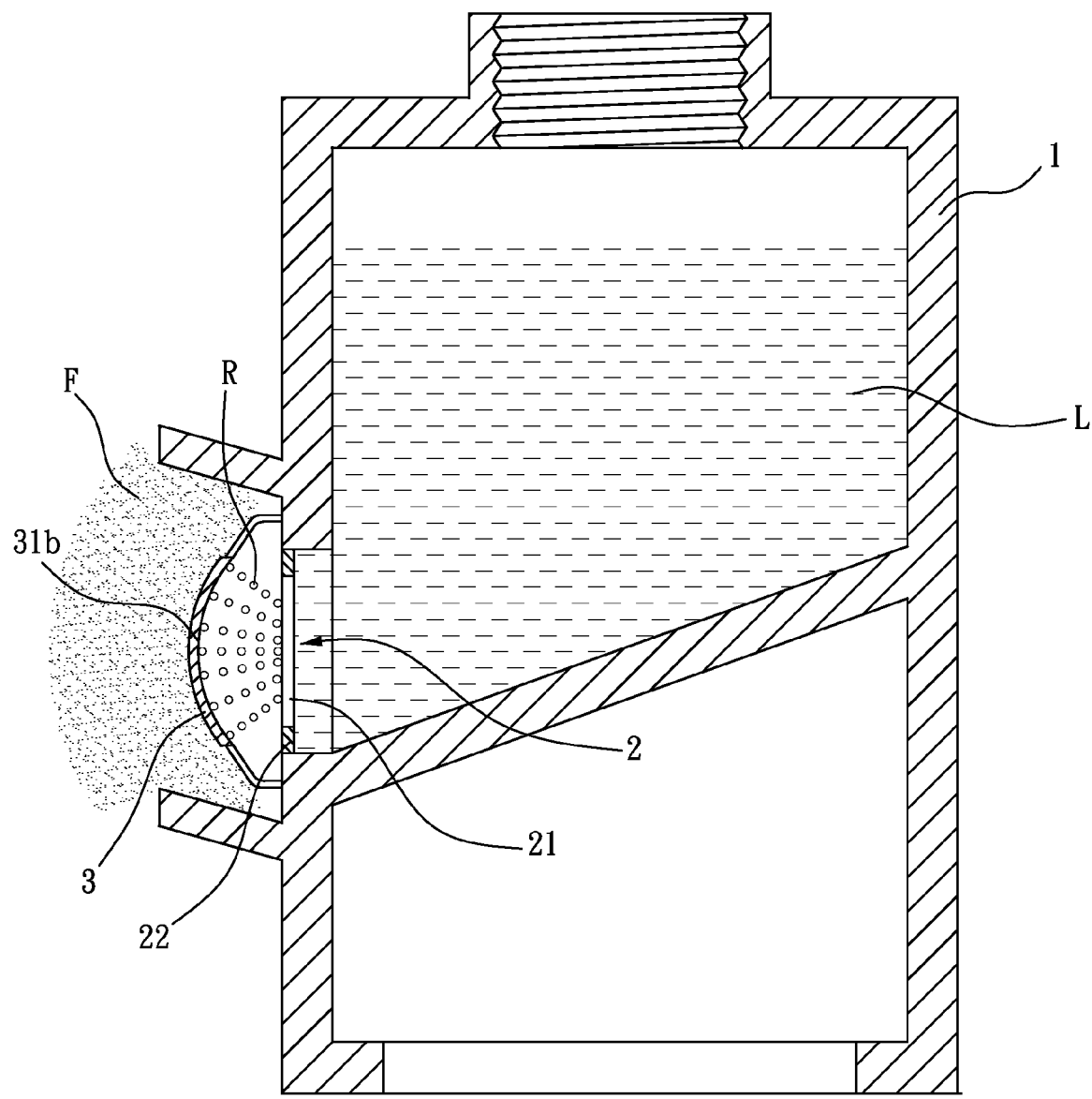
FIG. 3 shows a fragmentary cross-sectional view illustrating how a plurality of mist droplets are sprayed out in term of a plurality of micro mist droplets via a particle sorter employed in the liquid spray device of the present invention.

The spray module 2 is disposed in the discharge outlet 12 in the container 1, and is connected electrically to the drive source 4 such that the liquid medicine L forcefully collides against the discharge outlet 12 due to ultrasonic oscillation of the spray module 2, which is driven upon activation of the drive source 4, thereby spraying out a plurality of mist droplets. Note that the spray module 2 employed in this embodiment may have the structure similar to that disclosed by U.S. Pat. No. 6,629,646, which discloses an oscillating surface with a tapered apertures in contact with the fluid and/or U.S. Pat. No. 6,863,224, which discloses an ultrasonic horn oscillation member and a mesh member. The spray module disclosed in accordance with German Patent 102009001867 can also be utilized, the description of which are already known and hence a detailed explanation is omitted herein for the sake of brevity. As best shown in FIG. 3, the spray module 2 employed in the present embodiment includes a circular ultrasonic oscillator 22, in which, a mesh member 21 with a plurality of micro pores is disposed such that upon activation of the ultrasonic oscillator 22, the mesh member 21 vibrates at supersonic speed in an axial direction of the ultrasonic oscillator 22.

The drive source 4 in the lower reception space 10A in fact is a battery casing configured as a printed circuit (not visible) while a battery unit disposed in the space 10A. The printed circuit is electrically coupled with the ultrasonic oscillator 22 so that the power for activation of the ultrasonic oscillator 22 is supplied by the battery unit.

Figure 6:
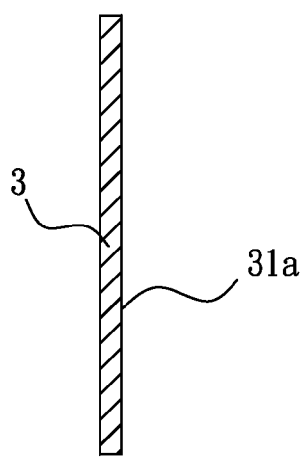
FIG. 6 shows a lateral side view of a planar particle sorter employed in the liquid spray device of the present invention.
Figure 7:
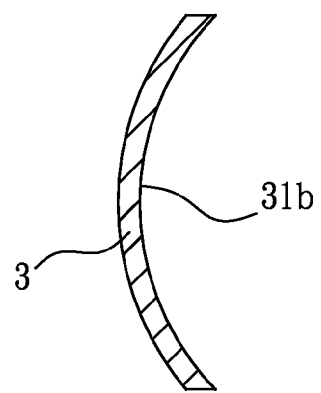
FIG. 7 shows a lateral side view of a convex particle sorter employed in the liquid spray device of the present invention.
Figure 8:
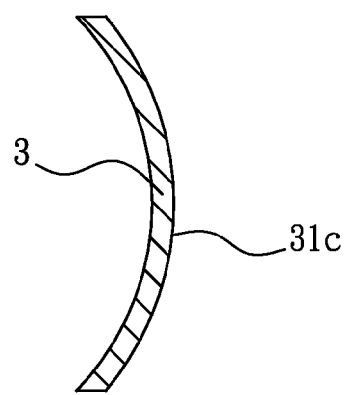
FIG. 8 shows a lateral side view of a concave particle sorter employed in the liquid spray device of the present invention.
Figure 9:
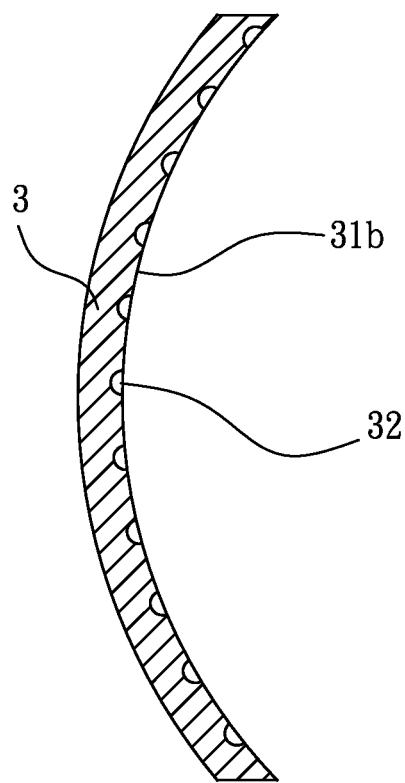
FIG. 9 shows a lateral side view of the concave particle sorter whose interior surface is formed with a plurality of recesses in the liquid spray device of the present invention.
Figure 10:
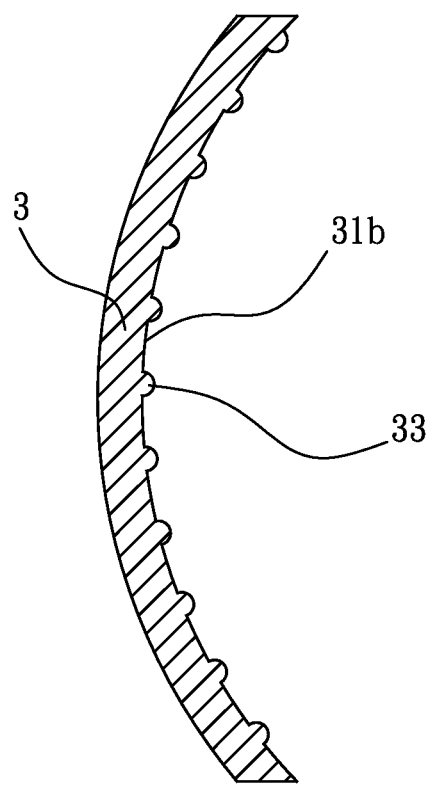
FIG. 10 shows a lateral side view of the concave particle sorter whose interior surface is formed with a plurality of protrusions in the liquid spray device of the present invention.

The particle sorter 3 is disposed downstream to a discharging direction of the liquid medicine L, is spaced from the spray module 2 at a predetermined distance to permit once against collision of the liquid medicine L during the discharging operation such that the plurality of mist droplets R are sprayed out through the particle sorter 3 in terms of a plurality of micro-mist droplets F along the discharging direction. The particle sorter 3 is formed with a plurality of micro pores. In this embodiment, the particle sorter 3 is a planar (or flat) plate having a flat surface 31a, as best shown in FIG. 6. Alternately, the particle sorter 3 is concave with respect to the spray module 2, has a concave interior surface 31b facing the spray module 2 (see FIG. 7). Moreover, the particle sorter 3 is convex with respect to the spray module 2, has a convex interior surface 31c facing the spray module 2 (see FIG. 8). Preferably, the concave interior surface 31b facing the spray module 2 is formed with a plurality of recesses 32, as best shown in FIG. 9. Alternately, the concave interior surface 31b facing the spray module 2 is formed with a plurality of protrusions 33, as best shown in FIG. 10. The surface area of the interior surface 31a, 31b and 31c, the number or size of the recess 32 or the protrusions 33, and the predetermined distance between the particle sorter 3 and the spray module 2 can be adjusted depending on the required size of the micro mist droplets F. For instance, the predetermined distance between the particle sorter 3 and the spray unit 2 can be adjusted to be equivalent to, less than or greater than the diameter of the particle sorter 3. Note that the above mentioned adjustment is conducted during the manufacturing process and the user can not do the adjustment of ones own accord. In this embodiment, the particle sorter 3 is mounted to the container 1 through a plurality of holding legs 34, which one end is attached to the periphery of the particle sorter 3 while the other end is fixed to the periphery of the discharge outlet 12 so as to space the particle sorter 3 at the predetermined distance relative to the spray module 2.

As best illustrated in FIG. 3, when the container 1 of the liquid spray device 1 of the present is filled with the liquid medicine L, the latter flows downward along the inclined bottom 101 due to the gravity to abut against the mesh member 21 provided with a plurality micro pores under fluid tension such that the liquid medicine L cannot penetrate through the micro pores of the mesh member 21. Under this condition, the mesh member 21 vibrates in axial direction of the discharge outlet 12 upon activation of the ultrasonic oscillator 22, the mesh member 21 vibrates at supersonic speed in an axial direction of the ultrasonic oscillator 22, the liquid medicine L in the container 1 is sprayed out through the micro pores of the mesh member 21 as a plurality of mist droplets R, which collide against the particle sorter 3 and are sprayed out again from the particle sorter 3 in terms of a plurality of micro-mist droplets F along the discharging direction. A patient suffering from chest ailment and nearby the liquid spray device of the present invention can breathe in the micro-mist droplets F in order to release the pain.

It is noted that each of the plurality of mist droplets R sprayed out from the mesh member 21 has a size greater than 5 μm. Thus, the expense of production the plurality of mist droplets R is relatively cheap However, in the present embodiment, a combination of the spray module 2, the particle sorter 3 and the mesh member 21 cooperatively can produce the plurality of mist droplets R again in term of the plurality of micro-mist droplets F, each having a MMAD size smaller than 5 μm owing to the fact that the particle sorter 3 has micro pores smaller than that of the mesh member 21 so that a patient can breathe in a majority portion of the micro-mist droplets F. Hence, overall expense of the liquid spray device of the present invention is reduced.

Figure 4:
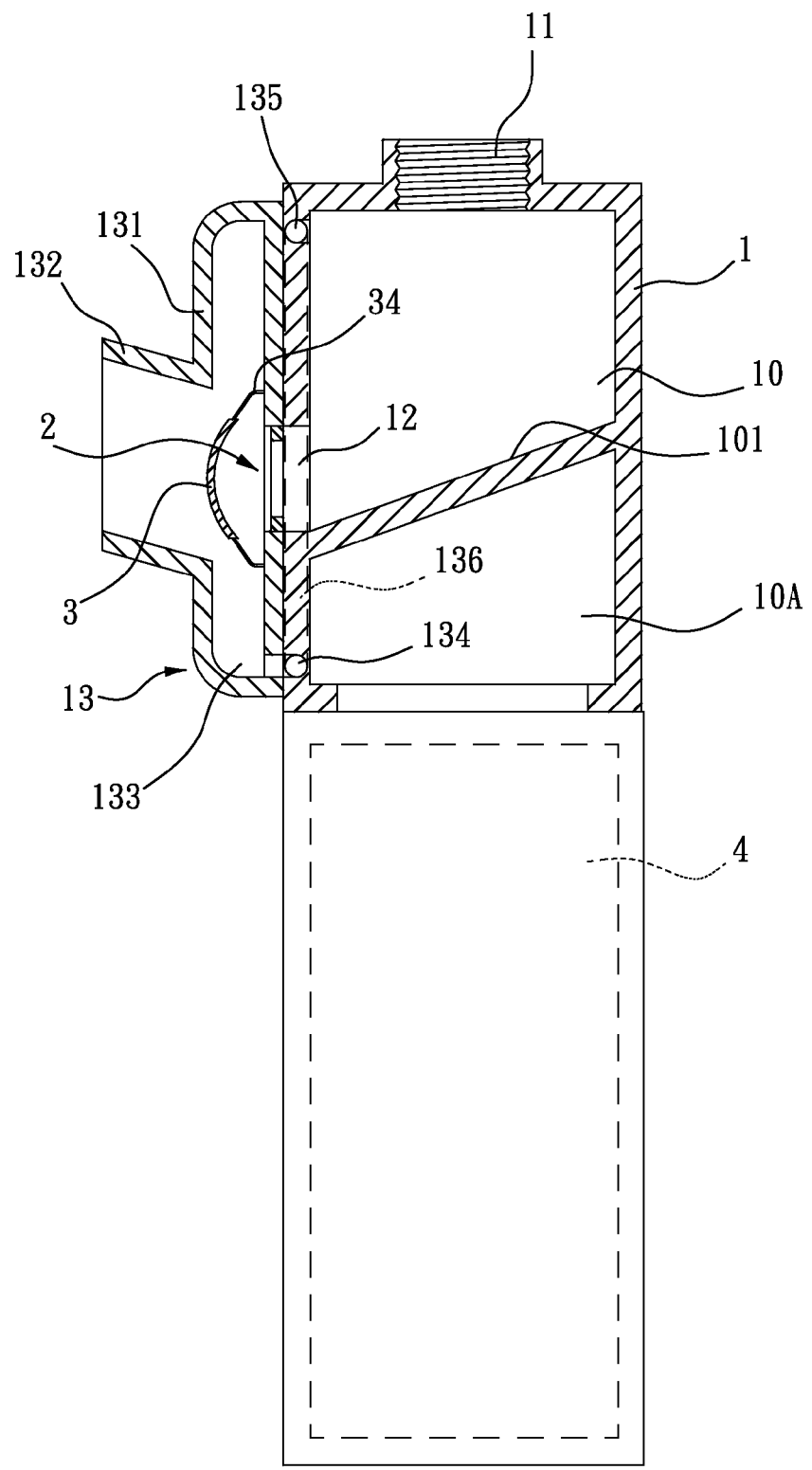
FIG. 4 shows a cross-sectional view of the liquid spray device of the present invention provided with a fluid recycle system and viewed from a lateral side thereof.

FIG. 4 shows a cross-sectional view of the liquid spray device of the present invention provided with a fluid recycle system 13 and viewed from a lateral side thereof. The motive of installing the fluid recycle system 13 in the spray device of the present invention is to economize and to make the outmost use of the liquid medicine L so as not to cause environment pollution. As illustrated, the container 1 further has a first opening 134 formed at a bottom most portion thereof (i.e., below the inclined bottom 101) and a second opening 135 formed at a topmost portion thereof and in spatial communication with the reception space 10. The fluid recycle system 13 includes a collection tube 131 fastened to the container 1, and having a lowest tube section 133 proximate to and in spatial communication with the first opening 134 and a connection pipe 136 interconnecting the first and second openings 134, 135 such that in case the discharge out 12 is biased by pressure of the liquid medicine L during the discharging operation, a siphon phenomenon is resulted due to vacuum of the reception space 10 to draw the plurality of mist droplets collected at the lowest tube section 133 back into the reception space 10 via the first opening 134, the connection pipe 136 and the second opening 135. In this embodiment, the connection pipe 136 is formed through a wall confining the reception space 10 in spatial communication with the discharge outlet 12 in addition to the first and second openings 134, 135. Preferably, the collection tube 131 has a dispensing tube section 132 inclined upward with respect to an axis of the discharging outlet 12 of the container 1.

Figure 5:
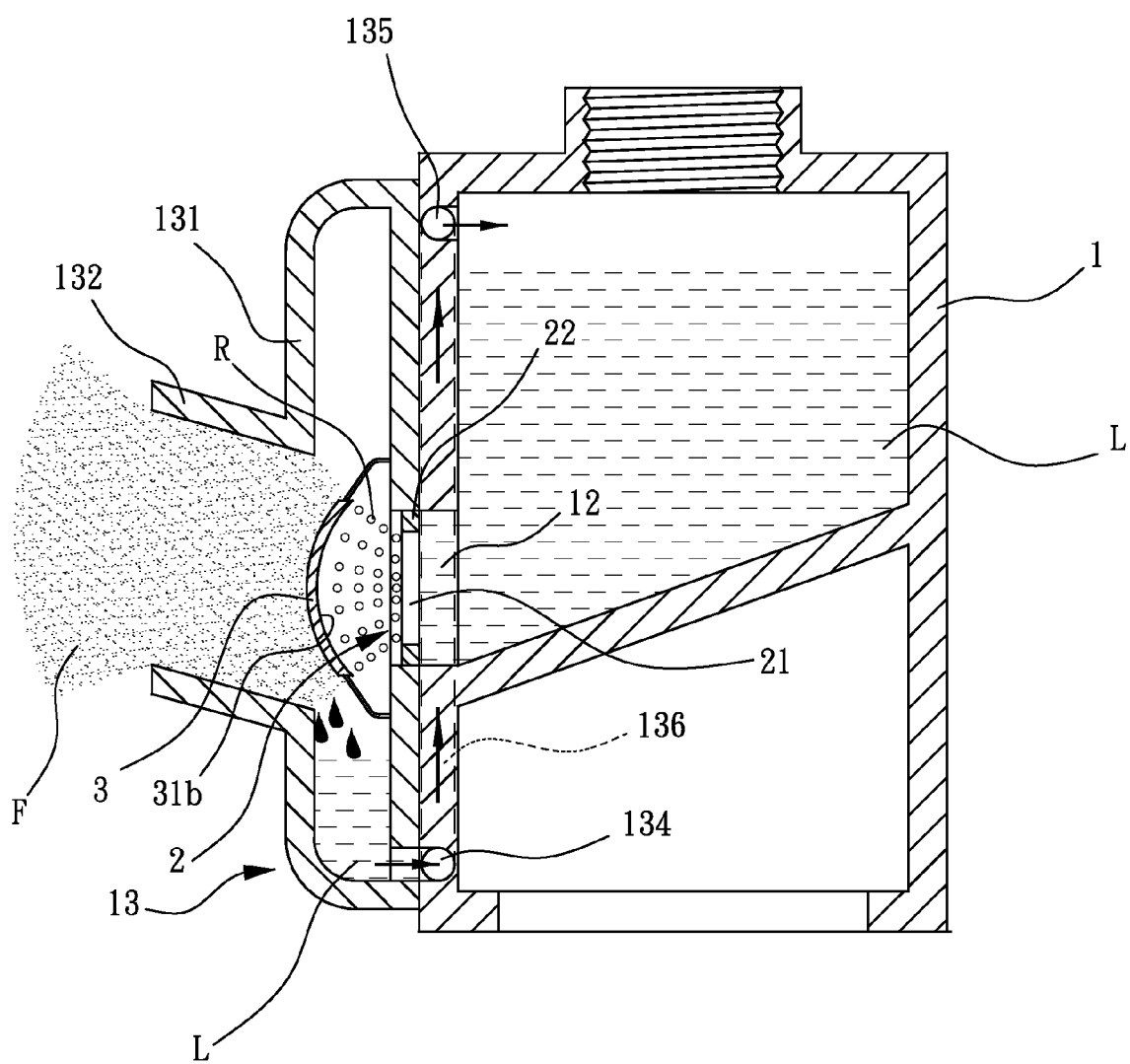
FIG. 5 shows a cross-sectional view illustrating how the recycle system functions in order to recycle the mist droplets collected in a collection tube back into a liquid container in the liquid spray device of the present invention.

FIG. 5 shows a cross-sectional view illustrating how the recycle system 13 functions in order to recycle the mist droplets collected in a collection tube back into the liquid container 1 in the liquid spray device of the present invention. As illustrated, during the discharging operation of the liquid medicine L from the container 1, the latter flows downward along the inclined bottom 101 due to earth gravity so that the liquid medicine L abuts against the micro pores in the mesh member 21 under tension. In the normal condition, the liquid medicine L cannot pass through the micro pores in the mesh member 21 owing to too small of the pores. Upon activation of the ultrasonic oscillator 22, the mesh member 21 vibrates at supersonic speed in an axial direction of the ultrasonic oscillator 22, the liquid medicine L in the container 1 is sprayed out through the micro pores of the mesh member 21 as a plurality of mist droplets R, which collide against the particle sorter 3 and are sprayed out again from the particle sorter 3 in terms of a plurality of micro-mist droplets F along the discharging direction. A portion of the mist droplets R and the micro-mist droplets F falls back into the lowest tube section 133 proximate to and in spatial communication with the first opening 134 and the connection pipe 136 interconnecting the first and second openings 134, 135 such that the discharge out 12 is biased by pressure of the liquid medicine during the discharging operation, a siphon phenomenon is resulted due to vacuum of the reception space 10 to draw the plurality of mist droplets R collected at the lowest tube section 133 back into the reception space 10 via the first opening 134, the connection pipe 136 and the second opening 135. Hence, there is no environmental pollution caused due to application of the liquid spray device of the present invention, which, in term, prevents undesired waste of the liquid medicine L.

While the invention has been described in connection with what is considered the most practical and preferred embodiments, it is understood that this invention is not limited to the disclosed embodiments but is intended to cover various arrangement included within the spirit and scope of the broadest interpretation so as to encompass all such modifications and equivalent arrangements.

What is claimed is:

1. A liquid spray device, comprising:

a container defining a reception space for receiving a liquid medicine therein, said container having a discharge outlet for discharging the liquid medicine to an exterior of the container, said container further having a first opening formed at a bottommost portion thereof and a second opening formed at a topmost portion thereof and in spatial communication with said reception space;

a spray module disposed in said discharge outlet, and being connected electrically to a driving source such that the liquid medicine forcefully collides against said discharge outlet due to ultrasonic oscillation of said spray module, thereby spraying out a plurality of mist droplets;

a particle sorter disposed downstream to a discharging direction of the liquid medicine, spaced from said spray module at a predetermined distance to permit further collision of the liquid medicine during a discharging operation such that said plurality of mist droplets are sprayed out through the particle sorter in terms of a plurality of micro-mist droplets along the discharging direction; and a recycle system that is installed within said container, that is adapted to collect said plurality of mist droplets and that is adapted to automatically transfer said plurality of mist droplets back into said liquid medicine for collecting in said reception space in said container, said recycle system including a collection tube fastened to said container and having a lowest tube section proximate to and in spatial communication with said first opening, and a connection pipe interconnecting said first and second openings such that in case said discharge outlet is biased by pressure of the liquid medicine during the discharging operation, a siphon phenomenon is resulted due to vacuum of said reception space to draw said plurality of mist droplets collected at said lowest tube section back into said reception space via said first opening, said connection pipe and said second opening.

2. The liquid spray device according to claim 1, wherein said collection tube has a dispensing tube section inclined upward with respect to an axis of said discharge outlet of said container.

3. The liquid spray device according to claim 1, wherein said particle sorter is planar, concave or convex with respect to said spray module.

4. The liquid spray device according to claim 3, wherein said particle sorter has a surface area greater than that of said spray module.

5. The liquid spray device according to claim 3, wherein said particle sorter has a surface area smaller than that of said spray module.

6. The liquid spray device according to claim 3, wherein said particle sorter has an interior surface facing said spray module and formed with a plurality of recesses.

7. The liquid spray device according to claim 3, wherein said particle sorter has an interior surface facing said spray module and formed with a plurality of protrusions.

8. The liquid spray device according to claim 3, wherein said predetermined distance is greater than a diameter of said particle sorter.

9. The liquid spray device according to claim 3, wherein said predetermined distance is smaller than a diameter of said particle sorter.

* * * * *